Figure 2:
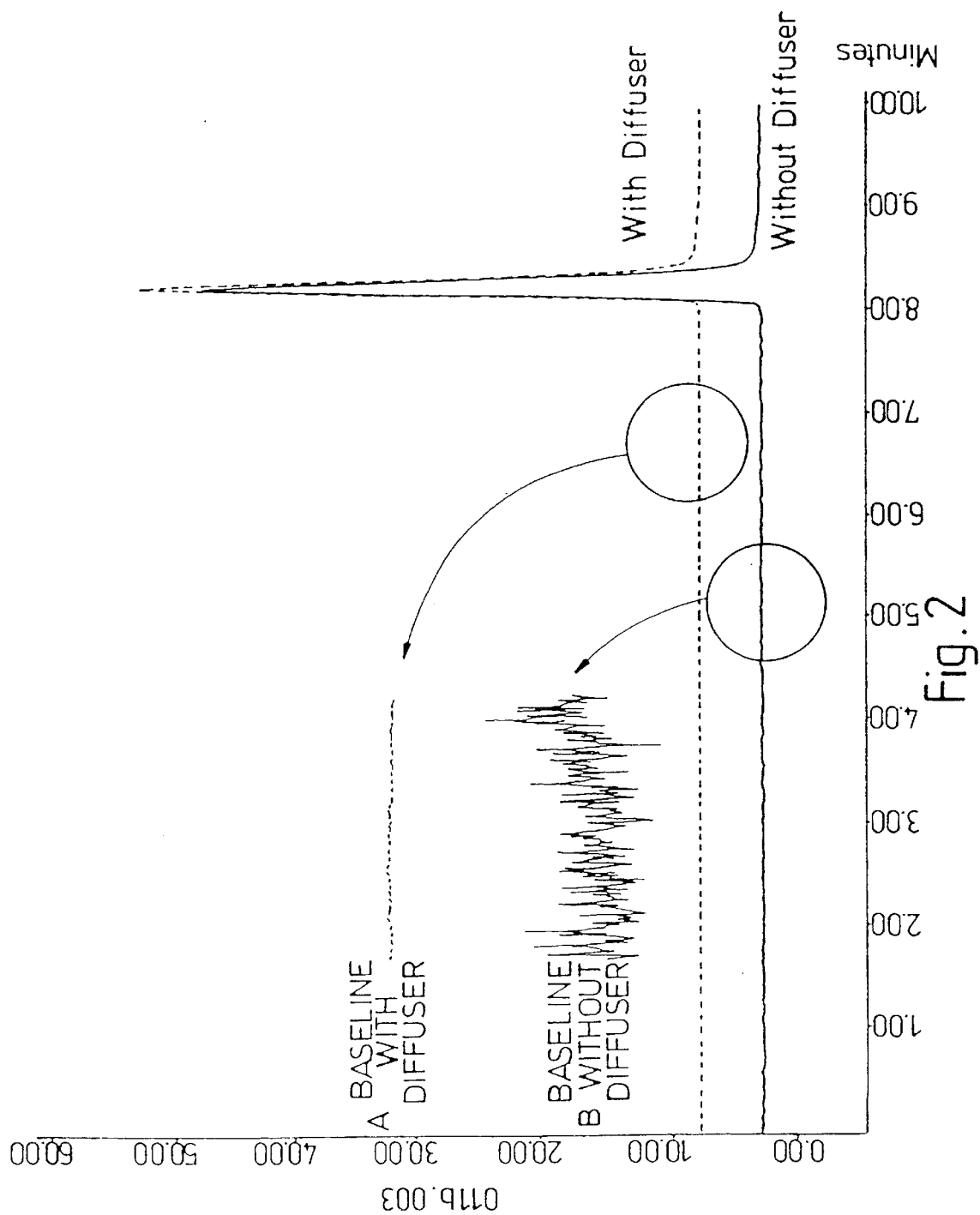

United States Patent
O'Donohue et al.

[19]

[11] Patent Number: 6,151,113
[45] Date of Patent: Nov. 21, 2000

[54] ELSD DIFFUSER

[75] Inventors: Stephen J O'Donohue, Shrewsbury; Frank P Warner, Church Stretton, both of United Kingdom

[73] Assignee: Polymer Laboratories Limited, Shropshire, United Kingdom

[21] Appl. No.: 09/051,825

[22] PCT Filed: Sep. 3, 1997

[86] PCT No.: PCT/GB97/02360

§ 371 Date: Oct. 5, 1998

§ 102(e) Date: Oct. 5, 1998

[87] PCT Pub. No.: WO98/10279

PCT Pub. Date: Mar. 12, 1998

[30] Foreign Application Priority Data

Mar. 9, 1997 [GB] United Kingdom ............. 9702360

[51] Int. Cl.[7] ........................................ G01N 21/00
[52] U.S. Cl. ................................. 356/338; 356/36
[58] Field of Search ........................ 356/338, 339, 356/336, 343, 36, 37, 340; 210/656, 198.2

[56] References Cited

U.S. PATENT DOCUMENTS

| | | | |
|---|---|---|---|
| 4,990,740 | 2/1991 | Meyer | 219/121.52 |
| 5,374,396 | 12/1994 | Blackford et al. | 422/73 |
| 5,454,274 | 10/1995 | Zhu | 73/863.12 |

OTHER PUBLICATIONS

"New! Alltech 500 ELSD–Your best Choice for Solving Tough Detection Problems"–Bulletin # 338A, Alltech Associates, Inc., Deerfield, IL, Jan. 1996.

Mourey, T.H., et al., "Principles of Operation of an Evaporative Light–Scattering Detector for Liquid Chromatograph", Anal. Chem (1984), 56:2427–2434.

Righezza, M., et al.., "Effects of the Nature of the Solvent and Solutes on the Response of a Light–Scattering Detector", Journal of Liquid Chromatography, (1988) 11:1967–2004.

Smith, R.M., et al., "Separation of Saturated and Unsaturated Fatty Acid Methyl Esters by Supercritical Fluid Chromatography on a Silica Column", Analyst, (May 1994), vol. 119, pp. 921–924.

Cocks, S., et al., "Analysis of Fatty Acid Methyl Esters by Using Supercritical Fluid Chromatography with Mass Evaporation Light Scattering Detection", Analytical Proceedings (Jan. 1991), vol. 28, pp. 11–12.

Dreux, M., et al., "Mesure de la diffusion de la lumiere sur des microparticules en phase gazeuse. Utilisations actuelles. Perspectives", Analysis, (1992), 20:587–595.

*Primary Examiner*—Frank G. Font
*Assistant Examiner*—Tu T. Nguyen
*Attorney, Agent, or Firm*—Peter J. Manus

[57] ABSTRACT

An evaporative light scattering detector (1) has a solvent nebuliser (4) through which an atomised spray of solute solvent solution passes, a heated evaporation chamber (5) and a detector system (6). A diffuser trapping device (7), supported by fine wires, is positioned in the evaporation chamber (5) at about two fifths of the height of the chamber from the top. The diffuser trapping device (7) is made from randomly coiled stainless steel ribbon which gives it a large surface area. The detection system (6) is positioned at the bottom of the evaporation chamber through which a beam of collimated light passes and is scattered by the solvent and detected by a light sensitive device (14). The diffuser trapping device (7) aids evaporation of the solvent and prevents large particles from travelling further down the evaporation chamber (5).

11 Claims, 4 Drawing Sheets

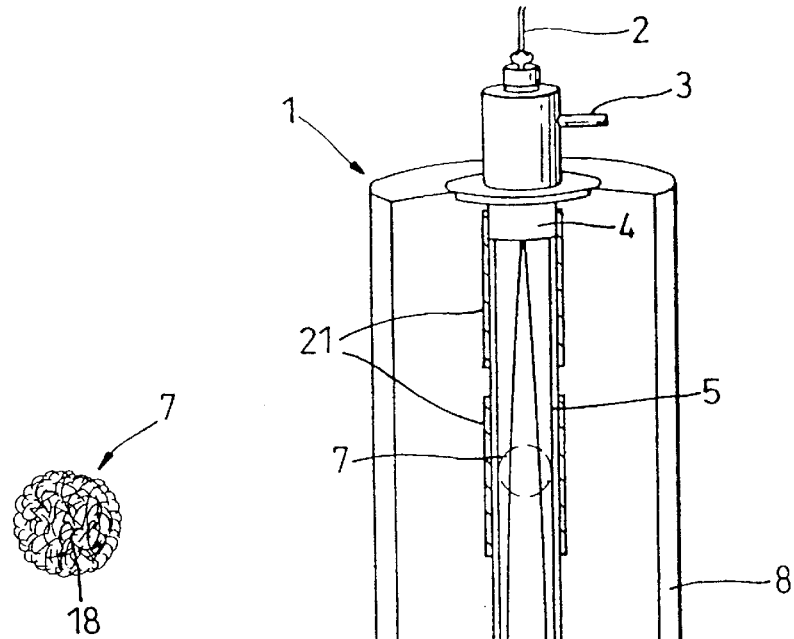
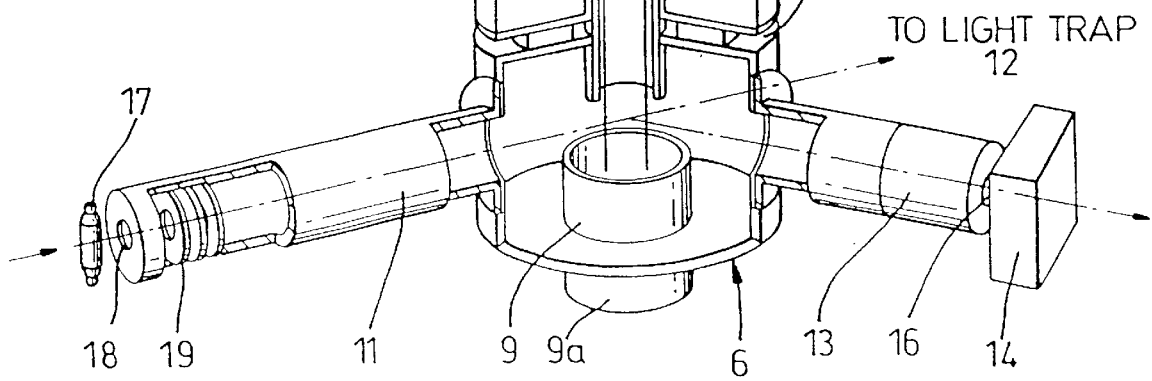
Fig. 1a
Fig. 1

ELSD DIFFUSER

This invention relates to a diffuser trapping device for use with a nebulisation system to produce a uniform atomised spray for use particularly, though not exclusively, in evaporative light scattering detectors (ELSD) for liquid chromatography.

Evaporative light scattering detectors are highly sensitive liquid chromatography detectors for non-volatile solutes dissolved in a volatile liquid stream (solvent). An ELSD operates in three stages—firstly nebulisation of the solvent occurs wherein the solvent or solvent/solute solution is atomised into a dispersion of droplets by a venturi jet operated by a jet of compressed air or an inert gas, such as nitrogen. Secondly the atomised spray passes into an evaporation chamber under the influence of the nebuliser gas flow, which may be fan assisted, that directs the atomised spray down the evaporation chamber and vents the exhaust at the rear of the instrument. The third stage is that of detection. Collimated light is passed through the instrument perpendicularly to the direction of gas flow at the base of the evaporation chamber. A light trap is positioned opposite the light source to eliminate internal reflections inside the body of the instrument. When a pure solvent is evaporated only its vapour passes through the light path and the amount of light scattered is small and constant. The present of a non-volatile solute causes a particle cloud to pass through the light path resulting in light scattering. The scattered light generates a signal response from a photomultiplier or other light sensitive device which is provided in the detection system. The quantity of light detected is dependent on both concentration and particle size distribution of the solute.

Evaporative light scattering detectors are used as concentration detectors in many liquid chromatography techniques such as gel permeation chromatography (GPC), high performance liquid chromatography (HPLC) and supercritical fluid chromatography (SFC).

Large droplets or large particles of solute that have not been fully nebulised and which may be present in the atomised spray can give excessive scattering to create a dramatic increase in background noise or noisy signal responses respectively and a decrease in the overall sensitivity of the detector. These large droplets or particles can arise from inadequate nebulisation and inefficient drying of the droplets.

By large droplets or particles it is meant those having a diameter equal to or greater than the wavelength of incident light.

With the above problems in mind we have now developed a diffuser-trapping device for use with a nebuliser system which will reduce the presence of undesirable large droplets or particles thereby reducing background noise and improving the sensitivity of the detector.

Accordingly from a first aspect the present invention provides an evaporative light scattering detector comprising a solvent nebuliser, a heated evaporation chamber and a detection chamber into which is directed a collimated light beam normal to the flow of nebulised solvent and a light sensitive device for detecting scattered light wherein a diffuser-trapping device is positioned within the evaporating chamber at a depth of between one-third and two-thirds of the height of the evaporating chamber and extends substantially across the full diameter of the chamber.

Accordingly from a second aspect the present invention comprises a diffuser-trapping device suitable for positioning within the heated area of the evaporation chamber of ELSD of the first aspect of the present invention comprising a three dimensional highly porous network of inert material preferably formed from a thermally conductive material which may have a fibrous construction.

The expression "highly porous" refers to a structure having a porosity of between 50 and 99% calculated from the void volume or free space relative to the total volume occupied by the diffuser trapping device.

The position of the diffuser trapping device depends upon the diameter of the spray exiting the nebuliser and is positioned at such a level within the evaporation chamber that the atomised particles are partially evaporated before they reach the diffuser trapping device. The optimum position being such that the spray hits the diffuser trapping device before it hits the heated walls of the evaporation chamber and is burnt out.

If the diffuser trapping device is positioned too close to the nebuliser the spray soaks into the diffuser which affects the temperature control and therefore the operation of the apparatus.

In a preferred embodiment the diffuser-trapping device is positioned at a depth of two fifths of the height of the evaporation chamber measured from the top of the chamber.

The diffuser-trapping device may comprise coiled ribbon or filaments of thermally conductive corrosion resistant metal most preferably the metal is thin stainless steel.

The metal ribbon is preferably coiled randomly, for example to form a highly porous tortuous network with a very high void content but without a direct line of sight pathway through the network. Other diffuser-trapping systems can be made from a random bundle of fibres or sintered metal or a series of overlapping porous meshes arranged so as to provide no line of sight passage through the network.

It is believed that the diffuser-trapping device functions in several ways:

Firstly the diffuser-trapping device prevents the larger and heavier particles or droplets from reaching the light scattering area by trapping them in the network whereas the smaller lighter particles, which are attached to the air flow, can travel through the tortuous network to the detector.

Secondly the diffuser provides a large surface area which contacts the heated walls of the evaporation chamber and gets hot giving a heated surface area which results in more efficient evaporation of the solvent in the droplets and particles containing solvent. It also aids the vaporisation of the large droplets and dries the particles trapped on the diffuser-trapping device.

Thirdly the diffuser directs the flow of atomised solute/solvent solution closer to the heated walls of the evaporation chamber which again aids evaporation of the solvent.

Each of the above functions of the diffuser-trapping device help to reduce the number of large droplets or particles which reach the light scattering chamber which, as has already been mentioned, reduces background noise and improves the sensitivity of the evaporative light scattering detector.

The diffuser-trapping device of the present invention has many applications and can be used in conjunction with a variety of systems to reduce the number of undesirable large solvent or solvent/solute particles in a nebulised or atomised spray including, but not limited to, evaporative light scattering detection.

The following applications are examples of use and improvements provided by the diffuser-trapping device as applied to an ELSD and in no way limit the applications to other systems, other types of ELSD or limit the applications of the ELSD.

1. High Performance Liquid Chromatography Applications (HPLC)

In carbohydrate chemistry, refractive index (RI) detectors are commonly used, however they are very unstable and temperature sensitive. The ELSD of the present invention overcomes these problems by providing an enhanced sensitivity and being stable to changes in external temperature.

In Peptide chemistry Ultraviolet absorption (UV) detectors are used, however the use of acetonitrile and trifluoroacetic acid as solvents can cause baseline deflections or drift and make integration difficult. The ELSD of the present invention gives level and non-drifting baseline throughout the chromatogram.

Many polar water soluble polymers are undetectable by UV detectors and show poor detection with an RI detector, however the ELSD of the present invention can detect these polymers to high sensitivity levels and maintains a level baseline.

The ELSD of the present invention can also be used in the detection of such substances as pharmaceuticals, surfactants, triglycerides preservatives and fat soluble vitamins.

2. Gel Permeation Chromatography Applications (GPC)

The ELSD of the present invention can operate at temperatures of up to 200° C. making it ideal for substances such as polyolefins. Enhanced sensitivity and maintaining a stable baseline are also beneficial in the analysis of polyolefins where other detection is difficult.

Figure 3:
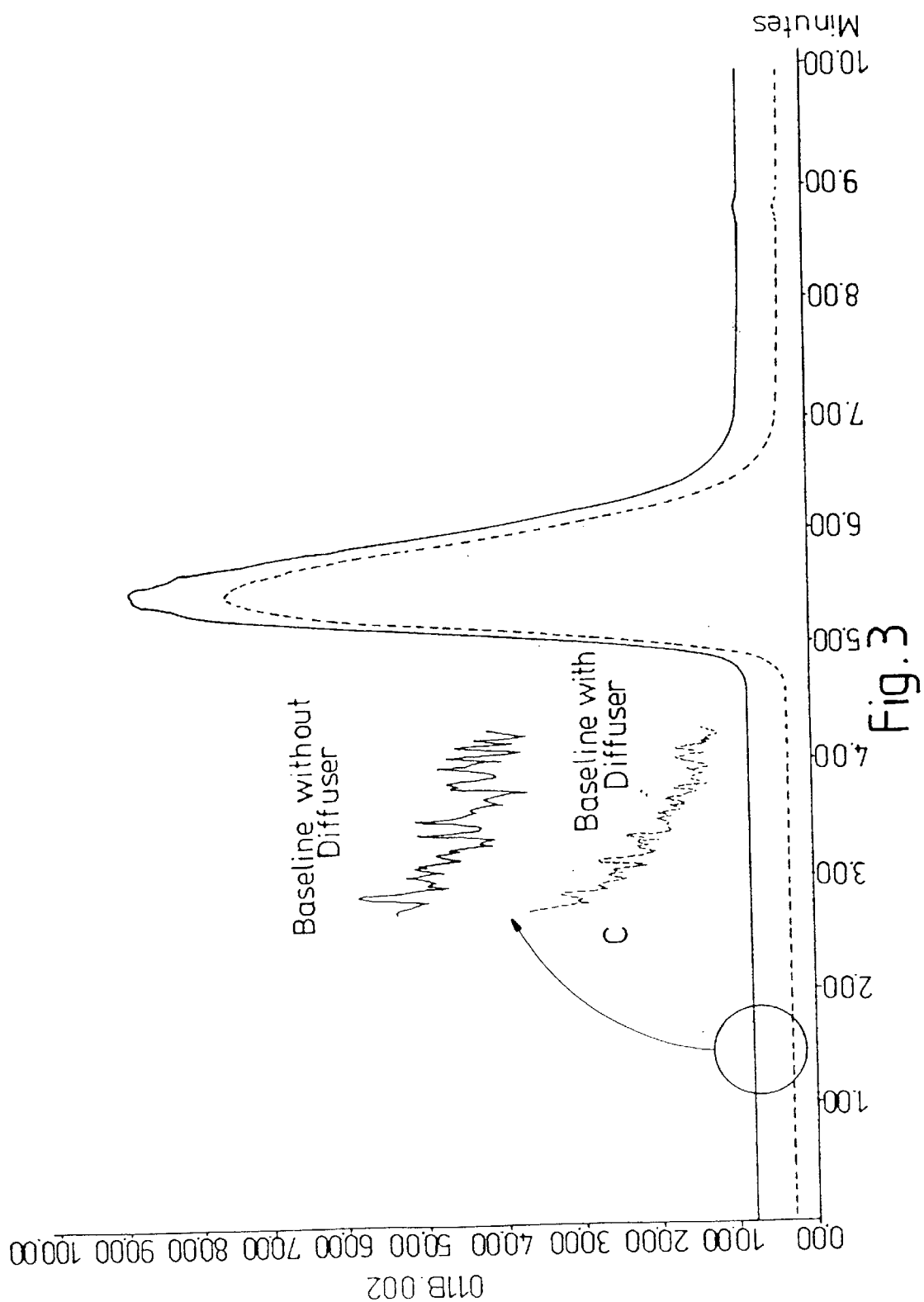

A preferred embodiment of the present invention will now be described by way of example only with reference to the figures of which:

FIG. 1 is a cross section of an evaporative light scattering detector incorporating the present invention, FIG. 1a is a view of the diffuser-trapping device of the present invention, FIG. 2 is a chromatogram for glucose obtained from an ELSD with and without a diffuser-trapping device, FIG. 3 is a chromatograph for polystyrene Mw 260000 g/mol obtained from an ELSD with and without a diffuser-trapping device.

Figure 4:
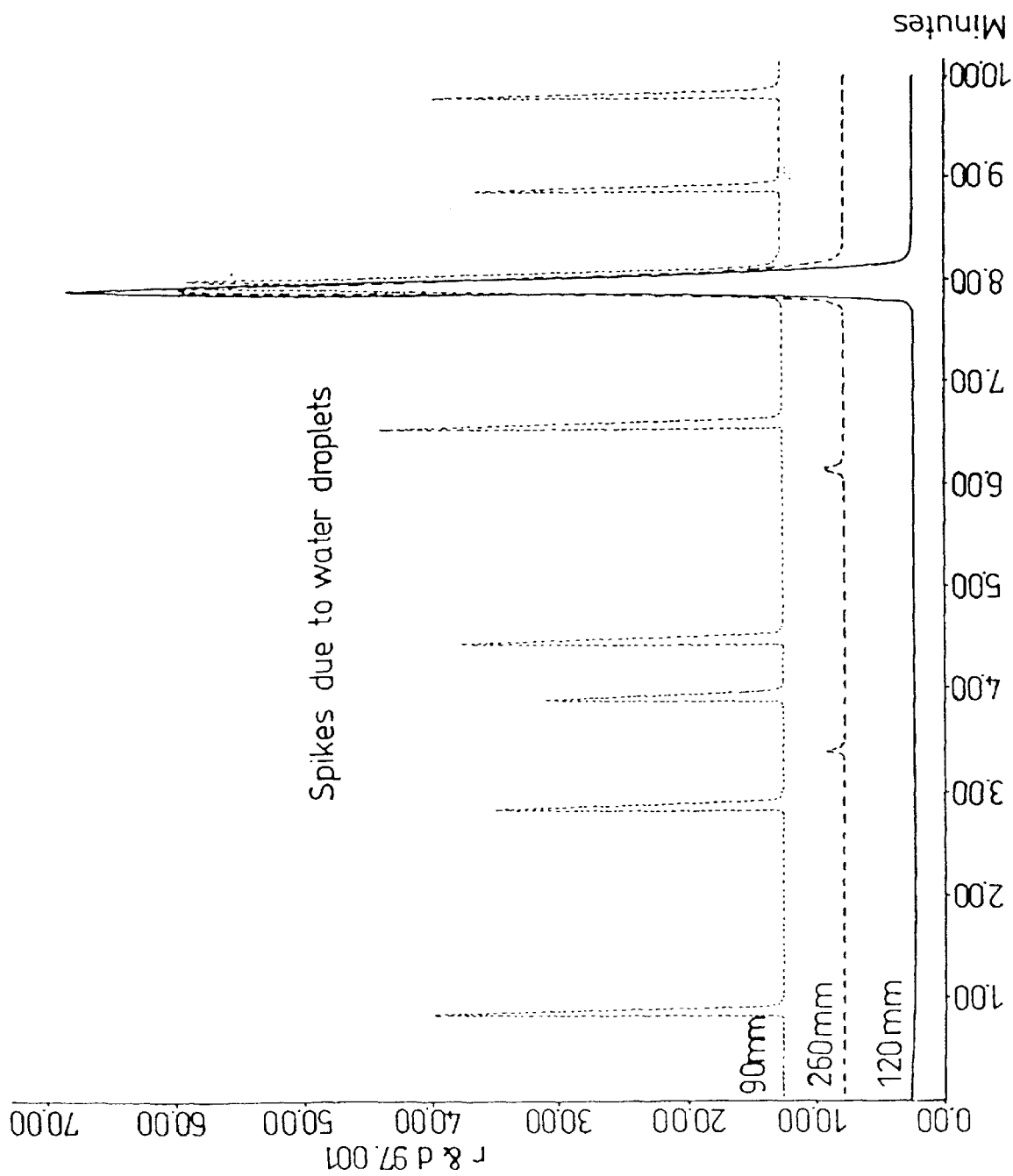

FIG. 4 is a chromatograph for glucose showing an overlay of the results obtained from an ELSD having the diffuser-trapping device positioned at three different heights.

FIG. 1 shows one example of an evaporative light scattering detector 1 having a solvent inlet 2, consisting of a small bore stainless steel capillary tube which can be attached to a column outlet. An inlet 3 for compressed air or inert gas is provided between the solvent inlet 2 and a solvent nebuliser 4 which is of a known type. A narrow cylindrical evaporation chamber 5 of length 330 mm and diameter 19 mm extends vertically downwards from the nebuliser 4 to the detection system 6. A diffuser-trapping device 7 is positioned inside the evaporation chamber 5 at a depth of h (100 mm), and is supported by fine stainless steel wires (not shown). A cylindrical casing 8 surrounds the nebuliser 4 and evaporation chamber 5. An exhaust chamber 9 is located in the base of the instrument, below the detection system 6, having a small fan (not shown) and an exhaust vent 9a.

The detector system 6 and exhaust chamber 9 are housed within a cylindrical casing 15. Two tubes 11 and 13 enter the casing 15 at 120° to each other and perpendicular to the evaporation chamber 5. Each tube 11, 13 has an aperture 10, 16 in its end remote from the casing 15. A light source 17 is provided outside tube 11 in front of aperture 10 and inside tube 11 a collimater 19 is positioned such that the light from source 17 passes through it. A photomultiplier detector 14 is provided at the end of tube 13. A light trap 12 is positioned opposite the light source.

FIG. 1a shows the diffuser-trapping device 7 which is constructed from a ribbon of stainless steel 18 which is randomly coiled to give an amorphous ball. The ribbon is 0.04 mm thick and 0.59 mm wide and the diffuser topping device has a weight of 0.9 gms.

In use the solvent is fed directly from the outlet of a chromatography column or other suitable means into the ELSD through a solvent inlet 2. The solvent flows into the nebuliser 4 where a venturi jet operated by compressed air, or an inert gas, entering the ELSD through the compressed gas inlet 3 atomises the solvent into a dispersion of droplets which then flow down into the evaporation chamber 5. The evaporation chamber 5 is heated by three band heaters situated around the exterior of the chamber (not shown) so that the droplets of atomised solvent evaporate during their passage down the chamber 5. The droplets have to pass through the diffuser 7 which is supported at a depth h (being 100 mm) from the top of the evaporation chamber. The diffuser-trapping device 7 has a large surface area and is heated by contact with the heated evaporation chamber in the vicinity of a band heater with the result being that it makes evaporation more efficient and acts as a trap to block large particles of solvent or solvent and solute from travelling further down the evaporation tube.

The small particles or droplets which are attached to the air pass through the diffuser-trapping device and flow down the remaining length of the evaporation chamber 5 and into the detector system 6. Light from source 17 passes through aperture 10 and through the collimater 19 in tube 11 the resultant collimated light then passes through the particle cloud flowing out of the evaporation chamber 5. The particle cloud scatters the light beam and scattered light travels along tube 13, out of aperture 16 into a photomultiplier detector 14 which generates a signal response. A light trap 12 eliminates internal reflections from the direct light beam within the instrument body. Exhaust venting occurs through exhaust chamber 9 and outlet 9a.

The effectiveness of the diffuser-trapping device 7 can be investigated by monitoring the signal to noise ratio of a solute response from the detector. A higher signal to noise ratio indicates a more effective diffuser-trapping device. Evaporative light scattering detection experiments using standard detectors not having a diffuser-trapping device as well as those incorporating the present invention were carried out on the following substances using the conditions specified.

Test probe 2 Glucose Mw 180 g/mol analysed in water

Chromatography Conditions:

Column: PL-GFC 8 μm 300Å 300×7.5 mm

Concentration: 1 mg/ml

Injection Volume: 50 μl

Solvent Flow: 1.0 ml/min

Detector Conditions:

Evaporation Temperature: 80° C.

Gas Flow: 7 L/min

Test probe 1 Polystyrene; MW 260000 g/mol, Mn 100000 g/mol analysed in tetrahydrofuran.

Chromatography Conditions:

Column: Plgel 5 μm MIXED-C 300×7.5 mm

Concentration: 1 mg/ml

Injection Volume: 50 μl

Eluent Flow: 1.0 ml/min

Detector Conditions

Evaporation Temperature: 40° C.

Gas Flow: 7 L/min

FIGS. 2 and 3 show the traces obtained when the above experiments were carried out, a significant reduction in background noise can be seen when the diffuser-trapping device of the present invention is used in conjunction with an ELSD. Areas of the baseline in both figures have been magnified to show the effect of the presence of the diffuser-trapping device on the background noise (areas A and B in FIG. 2 and area C in FIG. 3.).

Experiments were conducted to determine the optimum weight of the diffuser-trapping device by monitoring the signal to noise ratio (S/N) of the peak obtained for test probe 2 (Glucose) for diffuser-trapping devices with a weight ranging from 0.7 to 0.9 g. The results of this experiment are shown in table 1 below.

| Weight of Diffuser (g) | Signal (S) (mV) | Noise (N) (mV) | S/N |
| --- | --- | --- | --- |
| 0 | 448.3 | 2.14 | 209 |
| 0.701 | 734 | 0.69 | 1063 |
| 0.775 | 819 | 0.66 | 1240 |
| 0.800 | 819 | 0.60 | 1365 |
| 0.850 | 723 | 0.29 | 2424 |

The results show that a diffuser-trapping device reduces the noise significantly and the signal to noise ratio increases with increasing weight of the device up to approximately 1 gm.

The effect of the depth of the diffuser trapping device in the evaporation chamber can also be investigated by monitoring the signal to noise ratio at different diffuser depths.

Evaporative light scattering detection experiments using standard detectors incorporating the diffuser trapping device of the present invention at various positions were carried out under the following conditions. The performance was monitored from the signal (peak height) of a glucose and the short term noise measured on the base line.

Chromatography conditions:

Column PL-GFC 8 $\mu$m 300Å 300×7.5 mm

Eluent Water (HPLC grade)

Test Probe Glucose (0.1% w/v)

Injection Volume 50 $\mu$l

Eluent flow rate 1 ml/min

Detector conditions:

Temperature 80° C.

Gas Air (dried and filtered through 0.2 $\mu$m membrane)

Gas flow 7.5 L/min

The signal to noise ratio (S/N) of the test probe peak (glucose) was determined with the diffuser trapping device positioned at a depth of 40 mm, 90 mm, 120 mm, 155 mm and 260 mm from the top of the evaporation chamber. The results are shown in Table 2 below.

| Depth (mm) | Signal (S) (mV) | Noise (N) (mV) | S/N |
| --- | --- | --- | --- |
| 40 | No result | | |
| 90 | 447 | ~0.5 | 894 |
| 120 | 656 | 0.097 | 6763 |
| 155 | 591 | 0.118 | 5008 |
| 260 | 517 | 0.126 | 4103 |

FIG. 4 shows an overlay of the traces obtained when the above experiment was carried out.

The results show that the diffuser trapping device reduces the noise significantly and increases the signal to noise ratio with increasing depth of the position of the diffuser-trapping device from the top of the evaporation chamber up to approximately 120 mm.

Positioning the diffuser trapping device at a depth of 40 mm from the top of the evaporation chamber caused a heater error on the detector due to an excessive build up of water.

We claim:

1. An evaporative light scattering detector (ELSD) comprising:
    a solvent nebuliser,
    a heated evaporation chamber,
    a detection chamber into which is directed a collimated light beam normal to the flow of nebulised solvent,
    a light sensitive device for detecting scattered light, and
    a diffuser-trapping device positioned within said evaporation chamber at a depth of between one third and two thirds of the height of said evaporation chamber and extending substantially across the full diameter of said chamber,
    said diffuser-trapping device being formed of a material, and having a porous structure, such that it (i) traps large droplets of said solvent from said nebuliser in said porous structure and, (ii) enhances heat transfer from said heated evaporation chamber to said droplets to enhance their evaporation.

2. The ELSD according to claim 1 wherein said diffuser trapping device is positioned such that spray exiting said solvent nebuliser hits said diffuser trapping device before it hits the walls of said evaporation chamber.

3. The ELSD according to claim 1 wherein said diffuser trapping device is positioned at a depth of two fifths of the height of said evaporation chamber measured from the top.

4. A diffuser trapping device suitable for positioning with said heated area of the ELSD according to claim 1 comprising a three dimensional, highly porous network of inert material.

5. The diffuser trapping device according to claim 4 wherein the inert material has a fibrous construction.

6. The diffuser trapping device according to claim 4 wherein said inert material is coiled ribbon or filaments.

7. The diffuser trapping device according to claim 4 wherein said inert material is thermally conductive.

8. The diffuser trapping device according to claim 4 wherein said inert material is a corrosion resistant metal.

9. The diffuser trapping device according to claim 4 wherein said inert material is stainless steel.

10. The diffuser trapping device according to claim 6 wherein said ribbon is randomly coiled.

11. The diffuser trapping device according to claim 5 wherein the fibrous construction is a random bundle of fibres.

\* \* \* \* \*